United States Patent [19]

Duemmen

[11] Patent Number: Plant 7,359

[45] Date of Patent: Oct. 16, 1990

[54] GERANIUM PLANT NAMED 'DUELYR'

[76] Inventor: Guenter Duemmen, Dammweg 18-20, D-4134 Rheinberg 4, Fed. Rep. of Germany

[21] Appl. No.: 196,281

[22] Filed: May 20, 1988

[51] Int. Cl.[5] ..... A01H 5/00
[52] U.S. Cl. ..... Plt./68
[58] Field of Search ..... Plt./68

[56] References Cited

U.S. PATENT DOCUMENTS

PP 6,708 3/1989 Duemmen ..... Plt. 68

*Primary Examiner*—James R. Feyrer
*Attorney, Agent, or Firm*—Marks Murase & White

[57] ABSTRACT

A new and distinct Geranium plant known by the cultivar name Duelyr is characterized by a purple color, many inflorescences and double flowers, slight zonation, compact growth, and very early flowering.

1 Drawing Sheet

BACKGROUND OF THE NEW PLANT

The present invention comprises a new and distinct cultivar of Geranium, botanically known as *Pelargonium zonale,* and hereinafter referred to by the cultivar name Duelyr.

Duelyr is a product of planned breeding program which had the objective of creating new Geranium cultivars with purple-red colored flowers, robust dark foliage with slight zonation.

Duelyr was originated from a hybridization made in a controlled breeding program in Rheinberg, FRG, in 1983–1984. The female parent was an unnamed seedling. The male parent of Duelyr was an unnamed seedling.

Duelyr was discovered and selected as one flowering plant within the progeny of the stated cross by Guenter Duemmen in 1985 in a controlled environment in Rheinberg.

The first act of asexual reproduction of Duelyr was accomplished when vegetative cuttings were taken from the initial selection in July, 1985 in a controlled environment in Rheinberg by a technician working under formulations established and supervised by Guenter Duemmen. Horticultural examination of selected units initiated in October, 1985 has demonstrated that the combination of characteristics as herein disclosed for Duelyr are firmly fixed and are retained through successive generations of asexual reproduction.

Duelyr has not been observed under all possible environmental conditions. The phenotype may vary significantly with variations in environment such as temperature, light intensity, and day length. The following observations, measurements, and comparisons describe plants grown in Rheinberg under greenhouse conditions which approximate those generally used in commercial practice.

The following traits have been repeatedly observed and are determined to be basic characteristics of Duelyr which in combination distinguish this geranium as a new and distinct cultivar:

1. Purplered color;
2. Many inflorescences and double flowers;
3. Slight zonation;
4. Compact growth;
5. Very early begin of flowering.

Of the many commercial cultivars known to the present inventor(s), the most similar in comparison to Duelyr is Disco. Reference is made to attached Chart A which compares certain characteristics of Duelyr to those same characteristics of Disco. In comparison to Disco, Duelyr has slight zonation of foliage, reddish pedicel and a different color of the lower side of the upper petals.

The accompanying photographic drawing(s) show typical flower and foliage characteristics of Duelyr, with colors being as true as possible with illustrations of this type.

In the following description color references are made to The Royal Horticultural Society Colour Chart. The color values were determined between 10:00–2:00 p.m. on Feb. 10, 1988 under natural light conditions at Rheinberg.

Classification:
*Botanical.*—*Pelargonium zonale* cv. Duelyr.
*Commercial.*—Geranium.

INFLORESCENCE

A. Umbel:
*Average diameter.*—9 to 11 cm.
*Average depth.*—5 to 6 cm.
*Peduncle length.*—11 to 13.5 cm.
*Pedicel length.*—2.5–3 cm.

B. Corolla:
*Average diameter.*—5 to 6 cm.
*Form.*—Double.
*Color (general tonality from a distance of three meters).*—R.H.S. 57A.
*Color (abaxial).*—R.H.S. 52A.
*Color (adaxial).*—R.H.S. 58B.

C. Bud:
*Shape.*—*Elliptic.*
*Color (abaxial).*—Ca. R.H.S. 52A.
*Color (adaxial).*—Ca. R.H.S. 46D.

D. Reproductive organs:
*Androecium.*—Fertile, obdiplostemon, centrifugal dedouplement.
*Gynoecium.*—5-lobed stigma, pubescent, 5 carpels, coenocarp, hypogyn.

E. Spring flowering response period:
*FRG.*—50% of plants with at least one flower open 16 weeks after stick of unrooted cuttings.

F. Outdoor flower production: Very good.

G. Durability: Good.

H. Botanical description:

*Number of petals.*—8 to 10.

*Breadth of petals.*—1.6 cm.

*Length of petals.*—2.2 cm.

*Number of florets.*—5.3.

*Flower longevity.*—3 weeks.

*Flower placement above leaves.*—5.6 cm.

Outdoor flowering is continuous.

Florets have to be removed manually after end of flowering.

Propensity of the plant to set seed is only given with strong winds or insects strong engagement up to 4 per floret.

PLANT

A. Foliage:

*Form.*—Round.

*Margin.*—Bicrenated, Type 1.

*Color (abaxial).*—RHS 137A–B.

*Color (adaxial).*—RHS 138B.

*Color (zonation).*—RHS 139B.

*Tolerance of botrytis.*—Good.

B. General appearance and form:

*Internode length.*—Short to medium.

*Branching pattern.*—Good.

*Height.*—Medium to high.

C. Growing habitus:

*Height of leaves.*—18 cm.

*Length of shoots.*—6.5 cm.

*Diameter of plant.*—28 cm.

*Cuttings production.*—2.8 cuttings weekly between 4th and 9th months after pinching.

The plant shown has not been treated with a growth retardant; there are no pinching requirements.

CHART A

Comparison Between DUELYR and DISCO: Comparison is based on plants 16 weeks old in 12 cm pots.

| Differences: | DUELYR | DISCO |
|---|---|---|
| Zoning of leaves | Yes | No |
| Length of leaf blade | 7.5 cm | 9.8 cm |
| Color of leaves | Dark green | Light green |
| Length of peduncle | Short | Long |
| Size of umbel | Medium | Large |
| Floret | Large | Medium |
| Color of middle of upper side of petal | HCC 722 | HCC 724 |

What is claimed is:

1. A new and distinct cultivar of Geranium known as Duelyr, as described and illustrated, and particularly characterized by a purple color, many inflorescences and double flowers, slight zonation, compact growth, and very early flowering.

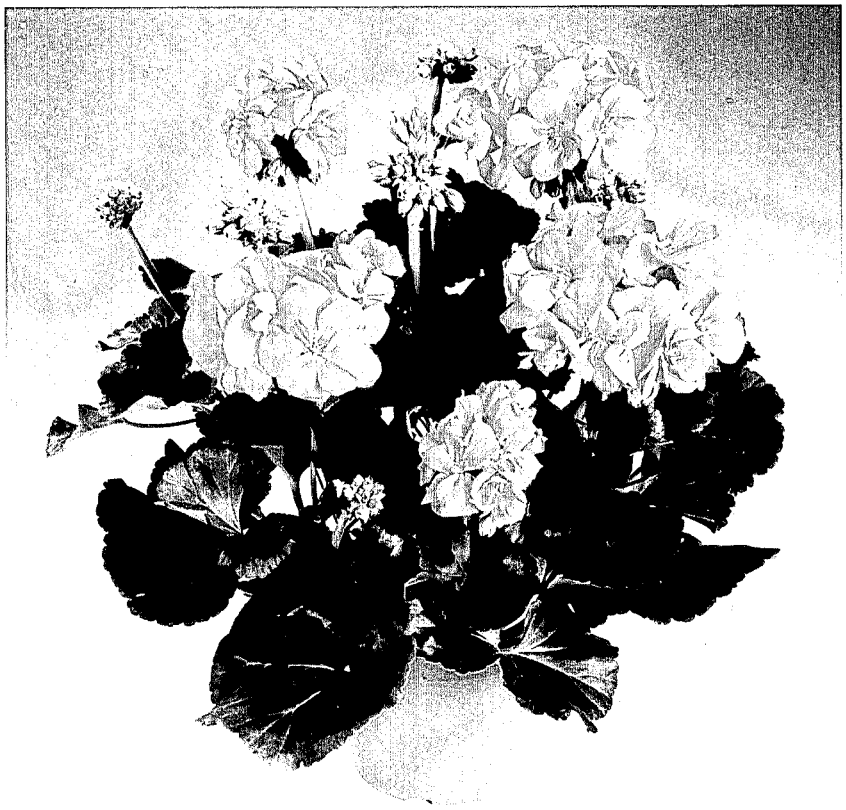

* * * * *